(12) United States Patent
Bhatnagar et al.

(10) Patent No.: US 7,034,022 B2
(45) Date of Patent: Apr. 25, 2006

(54) HEXAHYDROPYRIDAZINE-3-CARBOXYLIC ACID DERIVATIVES, PHARMACEUTICAL COMPOSITIONS CONTAINING SAME AND METHODS OF PREPARATION

(75) Inventors: Neerja Bhatnagar, Neshanic Station, NJ (US); Jean-Francois Gourvest, Clave Souilly (FR); Jacques Mauger, Tucson, AZ (US)

(73) Assignee: Aventis Pharma S. A., Antony (FR)

( * ) Notice: Subject to any disclaimer, the term of this patent is extended or adjusted under 35 U.S.C. 154(b) by 0 days.

(21) Appl. No.: 10/979,679

(22) Filed: Nov. 2, 2004

(65) Prior Publication Data

US 2005/0171346 A1    Aug. 4, 2005

Related U.S. Application Data

(63) Continuation of application No. PCT/FR03/01335, filed on Apr. 29, 2003.

(30) Foreign Application Priority Data

May 3, 2002   (FR) ................... 02 05573

(51) Int. Cl.
```
A01N 43/58    (2006.01)
A61K 31/50    (2006.01)
A61K 31/501   (2006.01)
C07D 237/00   (2006.01)
C07D 237/02   (2006.01)
```
(52) U.S. Cl. ............... 514/247; 514/252.01; 544/224; 544/238; 435/DIG. 34
(58) Field of Classification Search ............ 544/224, 544/238; 514/247, 252.01; 435/DIG. 34
See application file for complete search history.

(56) References Cited

U.S. PATENT DOCUMENTS 6,531,474 B1 *  3/2003  Wannamaker et al. ...... 514/248

2004/0176377 A1 *  9/2004  Holder et al. ............... 514/247
2005/0165017 A1 *  7/2005  Bhatnagar et al. ........ 514/235.5

FOREIGN PATENT DOCUMENTS

WO    WO 99/47545    9/1999
WO    WO 00/23421    4/2000

OTHER PUBLICATIONS

Schmidt et al, "Enantioselective Syntheses of (R)- and (S)-Hexahydropyridazine-3-Carboxylic Acid Derivatives" Synthesis, pp. 223-229 (Feb. 1996).*
Leung et al, Protease Inhibitors: Current Status and Future Prospects, Journal of Medicinal Chemistry, vol. 43, Issue 3, 2000, pp 305-341.

* cited by examiner

Primary Examiner—James O. Wilson
Assistant Examiner—Zachary C. Tucker
(74) Attorney, Agent, or Firm—Balaram Gupta

(57)  ABSTRACT

The present invention discloses and claims compounds of formula (I)

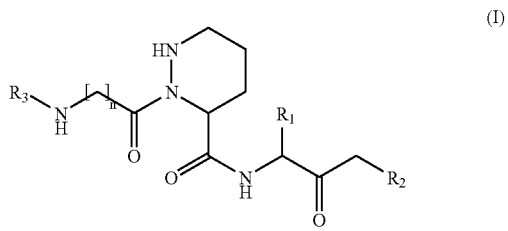

(I)

as inhibitors of proteases and kinases, method using said compounds of formula (I) for the prevention or treatment of certain cardiovascular, central nervous system, inflammatory, and bone diseases as well as infectious diseases and certain cancers. Combinatorial libraries of compounds of formula (I), pharmaceutical compositions and methods for preparation of combinatorial libraries and compounds of formula (I) are also disclosed and claimed.

19 Claims, No Drawings

HEXAHYDROPYRIDAZINE-3-CARBOXYLIC ACID DERIVATIVES, PHARMACEUTICAL COMPOSITIONS CONTAINING SAME AND METHODS OF PREPARATION

This application is a continuation of International Application No. PCT/FR03/01335 filed Apr. 29, 2003, which claims the benefit of priority of French Application No. 02 05573, filed May 3, 2002, which are incorporated herein by reference in their entirety.

BACKGROUND OF THE INVENTION

1. Field of the Invention

The invention relates to novel hexahydropyridazine-3-carboxylic acid derivatives, to the combinatorial libraries containing them, to the preparation thereof, to the use thereof as medicinal products, in particular as cathepsin K inhibitors, and also to the pharmaceutical compositions containing them.

2. Description of the Art

Metabolic enzymes such as proteases or kinases are enzymes that are widely distributed in the animal kingdom. By way of nonexhaustive examples, mention may be made, as bibliographical references for proteases, of the documents: "Methods in Enzymology XLII (1975)" and "Journal of Medicinal Chemistry" vol. 43 n° 3 (D. Leung, G. Abbenante and D. P. Fairlie) and for kinases, the document: "Methods in Enzymology", Vol 80(1981) (Academic Press Inc.).

Among the proteases capable of selectively catalyzing the hydrolysis of polypeptide bonds, mention may be made of the four main classes: aspartic protease, serine protease, cysteine protease and metalloprotease.

Aspartic proteases that may be mentioned include in particular HIV-1 protease, renin, plasmepsins and cathepsin D.

Serine proteases that may be mentioned include in particular thrombin, factcor Xa, elastase, tryptase, "convertase complements", and hepatitis C NS3 protease.

Among the cysteine proteases, three structurally distinct groups exist: the papain and cathepsin group, the ICE group (caspases) and the picornaviral group (similar to serine proteases in which the serine is replaced with a cysteine).

Thus, mention may in particular be made of cathepsin K, cathepsin B, cathepsin L, cathepsin S, caspases, rhinovirus 3C protease, and the papains and calpains.

Metalloproteases that may be mentioned include in particular angiotensin-converting enzyme, neutral endopeptidase and a mixture of the two, matrix metalloprotease and also tumor necrosis factor-α-converting enzyme.

These kinase or protease enzymes are involved in intercellular and intracellular catabolization and communication processes: they play an important role in a large number of diseases of different fields, such as in particular the cardiovascular field, oncology, the central nervous system, inflammation, osteoporosis, and also infectious, parasitic, fungal or viral diseases. For this reason, these proteins are targets of great interest for pharmaceutical research.

WO-A-0023421 describes compounds that are useful as inhibitors of ICE and, more generally, of enzymes of the cysteine protease type. Although its synthesis is not described, that document claims the compounds with the following formula:

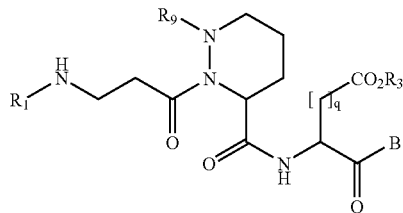

in which $R_1$ is a group of the aryl or heteroaryl type, $R_9$ is an alkyl, cycloalkyl(alkyl) or aryl(alkyl) group, and B is chosen from the groups $CH_2NHR_{16}$, $CH_2OCOaryl$ and $CH_2OCOheteroaryl$, the above aryl and heteroaryl groups possibly being substituted.

WO-A-9947545 describes compounds that are useful for the treatment for example of bone disorders (among which is mentioned osteoporosis). Although its synthesis is not described, that document claims the compounds with the following formula:

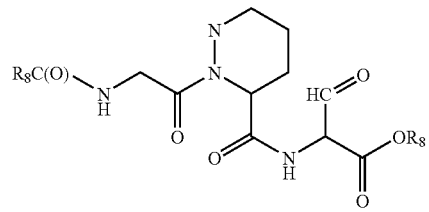

in which $R_8$ is an alkyl, cycloalkyl(alkyl), aryl(alkyl) or heteroaryl(alkyl) group, the above aryl and heteroaryl groups possibly being substituted.

None of the above documents teaches the present invention.

All of the aforementioned references are incorporated herein by reference in their entirety.

SUMMARY OF THE INVENTION

A subject of the present invention is thus a compound of formula (I):

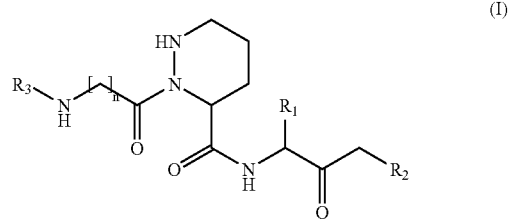

in which:
n is an integer from 0 to 6 inclusive;
$R_1$ represents a linear or branched alkyl group of 1 to 6 carbon atoms, an aryl group containing from 6 to 10 carbon atoms or an aralkyl group containing from 7 to 11 carbon atoms or a saturated or unsaturated, monocyclic or bicyclic, heterocyclic group,
these groups being optionally substituted with one to three substituents chosen from: OH, oxo, SH, $NH_2$, $NO_2$, cyano, carboxyl, carboxyl esterified with a $C_1$–$C_4$ alkyl or a $C_2$–$C_4$ alkenyl, carbamoyl, halogen, trifluoromethyl, linear or branched alkoxy containing from 1 to 6 carbon atoms, acyl containing from 2 to 6 carbon atoms, aryl or aralkyl, a saturated or unsaturated, monocyclic or bicyclic heterocycle, $R_2$ represents a group chosen from:
  with the carbon to which it is linked, the
  group C=$N_2$; or
  halogen; or
  hydroxyl;
  or a group chosen from
    —O—$(CH_2)_m$—R or S—$(CH_2)_m$—R
    —OC(O)—$(CH_2)_m$—R
    —NRR'
  in which
  m is an integer from 0 to 6 inclusive; it being possible for a double bond to be optionally present when m is greater than or equal to 2, it being possible for this chain to be substituted with a linear or branched alkyl group of 1 to 6 carbon atoms, an aryl group containing from 6 to 10 carbon atoms or an aralkyl group containing from 7 to 11 carbon atoms, or a saturated or unsaturated, monocyclic or bicyclic, heterocyclic group,
  R is one of the groups:
    hydrogen when m is other than 0;
    hydroxyl or thiol;
    cyano;
    linear or branched alkoxy containing from 1 to 6 carbon atoms or aryloxy or aralkoxy;
      the ring of the aryl or aralkyl radical being optionally substituted with one to three substituents chosen from: OH, SH, $NH_2$, $NO_2$, cyano, carboxyl, carboxyl esterified with a $C_1$–$C_4$ alkyl, carbamoyl, —NHC(O)O—$C_{1-4}$-alkyl, halogen, trifluoromethyl, linear or branched alkyl containing from 1 to 6 carbon atoms, linear or branched alkoxy containing from 1 to 6 carbon atoms, acyl containing from 2 to 6 carbon atoms, saturated or unsaturated, moncyclic or bicyclic heterocycle,
    cycloalkyl having from 3 to 6 carbon atoms;
    saturated or unsaturated, monocyclic or bicyclic, heterocyclic group;
      the ring of the heterocyclic radical being optionally substituted with one to three substituents chosen from: OH, oxo, SH, $NH_2$, $NO_2$, cyano, carboxyl, carboxyl esterified with a $C_1$–$C_4$ alkyl, carbamoyl, —NHC(O)O—$C_{1-4}$-alkyl, halogen, trifluoromethyl, linear or branched alkyl containing from 1 to 6 carbon atoms, linear or branched alkoxy containing from 1 to 6 carbon atoms, acyl containing from 2 to 6 carbon atoms, aryl or aralkyl, a saturated or unsaturated, monocyclic or bicyclic heterocycle,
      these alkyl or aryl or aralkyl or heterocyclic radicals being themselves optionally substituted with one to three substituents chosen from: OH, SH, $NH_2$, $NO_2$, cyano, carboxyl, carboxyl esterified with a $C_1$–$C_4$ alkyl, carbamoyl, halogen, trifluoromethyl,
    an aryl group containing from 6 to 10 carbon atoms or an aralkyl group containing from 7 to 11 carbon atoms,
      the ring of the aryl or aralkyl radical being optionally substituted with one to three substituents chosen from: OH, SH, $NH_2$, $NO_2$, cyano, carboxyl, carboxyl esterified with a $C_1$–$C_4$ alkyl, carbamoyl, —NHC(O)O—$C_{1-4}$-alkyl, halogen, trifluoromethyl, linear or branched alkyl containing from 1 to 6 carbon atoms, linear or branched alkoxy containing from 1 to 6 carbon atoms, acyl containing from 2 to 6 carbon atoms, a saturated or unsaturated, monocyclic or bicyclic heterocycle,
      these alkyl or heterocyclic radicals being themselves optionally substituted with one to three substituents chosen from: OH, SH, $NH_2$, $NO_2$, cyano, carboxyl, carboxyl esterified with a $C_1$–$C_4$ alkyl, carbamoyl, halogen, trifluoromethyl;
    a group $NR_4R_5$, $R_4$ being a hydrogen atom or a linear or branched alkyl group having from 1 to 6 carbon atoms, $R_5$ being a hydrogen atom or a linear or branched alkyl radical having from 1 to 6 carbon atoms or an aryl group;
  R', which is identical or different, has the same meaning as R, or, together with R and the nitrogen atom to which they are linked, forms a nitrogenous heterocycle,
    it being possible for this heterocycle to be substituted with one to three substituents chosen from: OH, SH, $NH_2$, $NO_2$, cyano, carboxyl, carboxyl esterified with a $C_1$–$C_4$ alkyl, carbamoyl, halogen, trifluoromethyl, linear or branched alkyl containing from 1 to 6 carbon atoms, linear or branched alkoxy containing from 1 to 6 carbon atoms, acyl containing from 2 to 6 carbon atoms, a saturated or unsaturated, monocyclic or bicyclic heterocycle, it being possible for the latter to be linked directly or by means of a group —C(O)— or —$CH_2$—C(O)—;
  $R_3$ represents —C(O)—$R'_3$, —C(O)—NH—$R'_3$, —C(S)—NH—$R'_3$ or —$SO_2$—$R'_3$,
    with $R'_3$ being a linear or branched alkyl group of 1 to 6 carbon atoms, an aryl group containing from 6 to 10 carbon atoms or an aralkyl group containing from 7 to 11 carbon atoms, or a saturated or unsaturated, monocyclic or bicyclic, heterocyclic group,
  said products of formula (I) being in any of the possible racemic, enantiomeric and diastereoisomeric isomer forms;
  and also the addition salts with inorganic and organic acids or with inorganic and organic bases of these products.

DETAILED DESCRIPTION OF THE INVENTION

According to one embodiment, n is 2.

According to one embodiment, $R_1$ represents an optionally substituted alkyl group.

According to one embodiment, $R_3$ represents an alkyl group.

According to one embodiment, $R_2$ represents a group chosen from:
  —O—$(CH_2)_m$—R or —S—$(CH_2)_m$—R
  —OC(O)—$(CH_2)_m$—R
  —NRR'
  in which
  m is an integer from 0 to 2 inclusive; it being possible for a double bond to be optionally present when m is equal to 2;

R is one of the groups:
- saturated or unsaturated, monocyclic or bicyclic, heterocyclic group;
  - the rings of these groups being optionally substituted,
- an aryl group containing from 6 to 10 carbon atoms or an aralkyl group containing from 7 to 11 carbon atoms,
  - the rings of these groups being optionally substituted, R', together with R and the nitrogen atom to which they are linked, form a nitrogenous heterocycle,
- it being possible for this heterocycle to be optionally substituted.

According to one embodiment, the compound according to the invention has the following stereochemistry:

[Chemical structure]

A subject of the invention is also the compound according to the invention, for its use as a medicinal product.

According to one embodiment, the medicinal product is intended for the prevention or treatment of diseases in which metabolic enzymes chosen from proteases and kinases are involved.

According to one embodiment, the medicinal product is intended for the prevention or treatment of diseases in which cathepsin K is involved.

According to one embodiment, the diseases to be prevented or treated are chosen from the group of diseases consisting of cardiovascular diseases, cancers, central nervous system diseases, inflammatory diseases, infectious diseases and bone diseases.

According to one embodiment, the diseases to be prevented or treated are osteoporosis, hypercalcemia, osteopenia, gingival diseases, arthritis, Paget's disease and bone cancers.

A subject of the invention is also a pharmaceutical composition containing, as active principle, at least one compound according to the invention, in combination with a pharmaceutically acceptable carrier.

A subject of the invention is also the use of a compound according to the invention, for preparing a medicinal product intended for the prevention or treatment of diseases in which metabolic enzymes chosen from proteases and kinases are involved.

A subject of the invention is also a combinatorial library of compounds according to the invention, in the form of a matrix of rank at least equal to 2, at least 2 ranks each comprising at least two compounds, preferably at least five, the compounds being individualized.

According to one embodiment, the combinatorial library is in the form of a matrix of rank equal to 3, the first rank corresponding to the group $R_1$, the second rank corresponding to the group $R_2$ and the third rank corresponding to the group $R_3$, each rank each comprising at least two compounds.

According to one embodiment, the combinatorial library is in the-form of a matrix of rank equal to 2, the first rank corresponding to the group $R_1$, the second rank corresponding to the group $R_2$, each rank comprising at least two compounds, the compounds being as claimed herein, the group $R_3$ having a predefined value.

According to one embodiment, the combinatorial library is such that:
the first rank corresponds to the group $R_1$, this group being chosen from the following residues:
isopropyl;
allyloxycarbonyl, or propionyl;
the second rank corresponding to the group $R_2$, this group being chosen from the following residues:
diazomethane;
pyridine-2,5-dicarboxylic acid 2-methyl ester;
3-pyridin-2-yl-4,5-dihydroisoxazole-5-carboxylic acid;
(5-methyl-2,4-dioxo-3,4-dihydro-2H-pyrimidin-1-yl) acetic acid;
2-pyrazinecarboxylic acid;
[4-(2-oxo-2-pyrrolidin-1-ylethyl)piperazin-1-yl]acetic acid;
diazomethane;
pyridine-2,5-dicarboxylic acid 2-methyl ester;
3-pyridin-2-yl-4,5-dihydroisoxazole-5-carboxylic acid;
(5-methyl-2,4-dioxo-3,4-dihydro-2H-pyrimidin-1-yl) acetic acid;
2-pyrazinecarboxylic acid;
[4-(2-oxo-2-pyrrolidin-1-ylethyl)piperazin-1-yl]acetic acid;
benzoic acid;
2-pyridinecarboxylic acid;
3-(1H-imidazol-4-yl)acrylic acid;
3-pyridin-2-ylacrylic acid;
5-methyl-2-pyrazinecarboxylic acid;
5-methyl-4-isoxazolecarboxylic acid;
1-isoquinolinecarboxylic acid;
benzo[1,2,5]oxadiazole-5-carboxylic acid;
5-isoxazolecarboxylic acid;
thiophen-3-ylacetic acid;
2,5-dichlorobenzoic acid;
chlorine;
3-quinolinecarboxylic acid;
5-cyanonicotinic acid;
6-methylnicotinic acid;
3-pyrimidin-2-ylpropionic acid;
1H-indole-5-carboxylic acid;
2-pyridin-3-ylfuran-3-carboxylic acid;
4'-ethylbiphenyl-4-carboxylic acid;
pyridine-2,4-dicarboxylic acid 2-methyl ester;
5-bromonicotinic acid;
hydroxyl;
2-methyl-4-oxo-1,2,3,4-tetrahydroquinazoline-2-carboxylic acid;
5-methyl-1H-pyrazole-3-carboxylic acid;
3-(cyanomethylmethyl)benzoic acid;
5-hydroxymethylisoxazole-3-carboxylic acid;
4-fluoro-2-methylbenzoic acid;
4-oxo-4-thiophen-2-ylbutyric acid;
4-(4-tert-butoxycarbonylaminopiperidin-1-yl)-4-oxobut-2-enoic acid;
3-(4-tert-butoxycarbonylaminophenyl)acrylic acid;
(4-butoxyphenoxy)acetic acid;
3-benzoimidazol-1-yl-3-phenylacrylic acid;

4-oxo-1,2,3,4-tetrahydronaphthalene-2-carboxylic acid;
2-thiophen-2-ylpropionic acid;
propynoic acid;
the group $R_3$ being isovaleryl.

According to one embodiment, the invention provides a combinatorial library of compounds according to the invention in the form of a set of compounds, these compounds being individualized, the set comprising at least 4 distinct compounds.

According to one embodiment, these compounds are individualized and the set comprises the compounds in which the groups $R_1$, $R_2$ and $R_3$ are as defined above.

A subject of the invention is also the use of a combinatorial library according to the invention, as a tool for screening for medicinal products intended for the prevention or treatment of diseases in which metabolic enzymes chosen from proteases and kinases are involved.

The products of the present invention as defined above and below have inhibitory properties with respect to metabolic enzymes as defined above, in particular with respect to kinases or proteases such as in particular cysteine proteases or serine proteases.

The products of the invention may thus in particular be useful in the prevention or treatment of diseases in which such metabolic enzymes are involved, such as certain cardiovascular diseases, central nervous system diseases, inflammatory diseases, bone diseases such as, for example, osteoporosis, infectious diseases requiring anti-infectious agents for the treatment thereof, or else certain cancers.

In the products of formula (I) and in the following text:
the bivalent group represented by —$(CH_2)_n$— may be linear or branched;
the term "aryl containing from 6 to 10 carbon atoms" denotes an unsaturated radical, comprising one or two fused rings, optionally containing one to three hetero atoms chosen from nitrogen, oxygen and sulfur. Mention may be made of: phenyl, naphthyl;
the term "aralkyl containing from 7 to 11 carbon atoms" denotes an aryl radical as defined above, linked by means of a linear or branched alkyl radical, this alkyl radical having from 1 to 5 carbon atoms. Mention may in particular be made of benzyl;
the terms "alkoxy", "aryloxy" and "aralkyloxy" indicate the presence of a terminal oxygen on the alkyl, aryl or aralkyl group;
the term "monocyclic heterocyclic radical" denotes a saturated or unsaturated radical consisting of 5 or 6 ring members, such that one or more of the ring members represents an oxygen, sulfur or nitrogen atom: such a heterocyclic radical thus denotes a carbocyclic radical containing one or more hetero atoms chosen from oxygen, nitrogen or sulfur atoms, it being understood that the heterocyclic radicals may contain one or more hetero atoms chosen from oxygen, nitrogen or sulfur atoms and that, when these heterocyclic radicals comprise more than one hetero atom, the hetero atoms of these heterocyclic radicals may be identical or different. Mention may in particular be made of the radical: dioxolane, dioxane, dithiolane, thiooxolane, thiooxane, morpholinyl, piperazinyl, piperazinyl substituted with a linear or branched alkyl radical containing at most 4 carbon atoms, piperidyl, thienyl such as 2-thienyl or 3-thienyl, furyl such as 2-furyl, pyrimidinyl, pyridyl such as 2-pyridyl, 3-pyridyl or 4-pyridyl, pyrimidyl, pyrrolyl, thiazolyl, isothiazolyl, diazolyl, thiadiazolyl, triazolyl, free or salified tetrazolyl, thiadiazolyl, thiatriazolyl, oxazolyl, oxadiazolyl, or 3- or 4-isoxazolyl. Mention may most particularly be made of the radicals: morpholinyl, thienyl such as 2-thienyl or 3-thienyl, furyl such as 2-furyl, tetrahydrofuryl, thienyl, tetrahydrothienyl, pyrrolyl, pyrrolinyl, pyridyl and pyrrolidinyl;
the term "bicyclic heterocyclic radical" denotes a saturated or unsaturated radical consisting of 8 to 12 ring members, such that one or more of the ring members represents an oxygen, sulfur or nitrogen atom, and in particular condensed heterocyclic groups containing at least one hetero atom chosen from sulfur, nitrogen and oxygen, for example benzothienyl such as 3-benzothienyl, benzothiazolyl, quinolyl, tetralone, benzofuryl, benzopyrrolyl, benzimidazolyl, benzoxazolyl, thionaphthyl, indolyl or purinyl.

The compounds of formula (1) may be converted into salts (salified) by means known to those skilled in the art, among which mention may be made, for example, of:
among the salt forming compounds, inorganic bases such as, for example, an equivalent of sodium, of potassium, of lithium, of calcium, of magnesium or of ammonium or organic bases such as, for example, methylamine, propylamine, trimethylamine, diethylamine, triethylamine, 1a N,N-dimethylethanolamine, tris(hydroxymethyl)aminomethane, ethanolamine, pyridine, picoline, dicyclohexylamine, morpholine, benzylamine, procaine, lysine, arginine, histidine, N-methylglucamine;
the addition salts with inorganic or organic acids of the products of formula (1) may be, for example, the salts formed with hydrochloric acid, hydrobromic acid, hydroiodic acid, nitric acid, sulfuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, the alkylmonosulfonic acids such as, for example, methanesulfonic acid, ethanesulfonic acid, propanesulfonic acid, the alkyldisulfonic acids such as, for example, methanedisulfonic acid, alpha, beta-ethanedisulfonic acid, the arylmonosulfonic acids such as benzenesulfonic acid and the aryldisulfonic acids.

It may be recalled that stereoisomerism can be defined in its broad sense as compounds that have the same structural formulae, but in which the various groups are arranged differently in space, such as for example, monosubstituted cyclohexanes in which a substituent may be in the axial or equatorial position, and the various possible rotational conformations of ethane derivatives. However, another type of stereoisomerism exists, due to the different spatial arrangements of fixed substituents, either on double bonds or on rings, which is often referred to as geometric isomerism or cis-trans isomerism. The term "stereoisomers" is used in the present application in its broadest sense, and therefore includes all the compounds indicated above.

As used herein, the term "rank" defines the number of dimensions for a matrix. The aforesaid matrix is comprised of at least two ranks or dimensions, wherein each rank is further comprised of at least two substituent groups as defined for one of the Markush groups of a compound of formula (I) of the invention, such as for example, $R_1$, $R_2$, $R_3$ or the like Markush groups. It is understood that the aforesaid matrix represents "individualized" or single compounds as defined by the combination of individual matrix row and column substituent groups, but mixtures of compounds may also be represented.

Combinatorial Library of Compounds According to the Invention

A subject of the present invention is thus also combinatorial libraries. These combinatorial libraries are in particular in the form of matrices of variable rank, the rank being at least 2, at least 2 ranks containing at least 2 compounds, each compound being individualized.

It is understood that these matrices can be made available in a form which is not necessarily of the same rank; it is thus possible to obtain a matrix of rank 3 in the form of plates with test species, the plates being of order 2. It is also understood that the matrices, for example of rank 3, when they are available in a form of order 3 or less, are not necessarily ordered.

The invention also covers the combinatorial libraries in the form of sets comprising a plurality of compounds according to the invention, each compound being individualized. This set of compounds comprises in particular plates with wells each comprising a compound according to the invention. These sets comprise at least 4 individualized compounds according to the invention.

The combinatorial libraries according to the invention are in particular discrete.

The combinatorial libraries comprise in general a large number of compounds, typically of the order of about a hundred or of about a thousand.

These combinatorial libraries are used as a search tool for the purpose of screening for medicinal products. The compounds making up the library show the pharmacological properties mentioned below.

Chemical Synthesis and Pharmacology

1. Chemical Methods According to the Invention

In the method according to the invention, the compounds are prepared in the form of combinatorial libraries, as indicated above. It is also possible to prepare them conventionally by carrying out the method, compound by compound.

The method according to the invention thus comprises the following steps:

(i) reaction of a compound of formula (II):

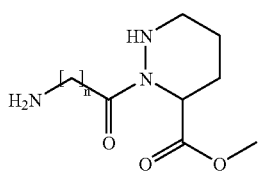

II in which n has the value indicated above, with a reactant that is a precursor of $R_3$, this precursor being the corresponding anhydride, acid chloride, sulfonyl chloride, carbamoyl chloride, chloroformate, isocyanate or isothiocyanate of the group $R_3$, this precursor having the meaning corresponding to that of $R_3$ as defined above in a compound of formula (III):

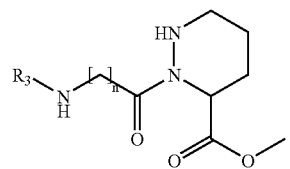

III (ii) saponifying the compound of formula III to its corresponding 3-carboxylic acid of formula (IIIa);

(iii) reacting the compound of formula IIIa with a compound of formula IV below:

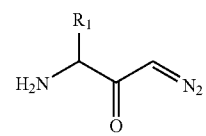

IV in which $R_1$ has the meaning indicated above, so as to produce a compound of formula V:

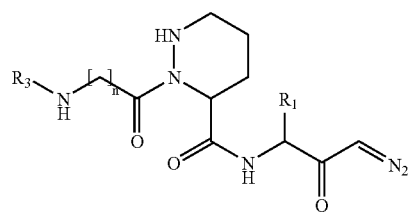

V (iv) halogenating the compound V to a compound of formula (VI):

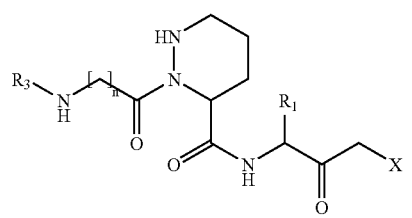

VI in which X is a halogen atom;

(v) reacting the compound of formula VI with a compound of formula $R_2H$, $R_2$ having the meaning as indicated above, to form the desired compound of formula I.

The latter reaction can be omitted when the compound of formula I corresponds to that of formula VI (in the case of $R_2$ halogen) or can be replaced with an equivalent step of substitution of the halogen X when $R_2$ is another halogen or hydroxyl.

The last two steps can be omitted when the desired compound is that in which $R_2$, with the carbon to which it is linked, forms the group $C=N_2$.

These reactions (i) to (v) are carried out under conventional conditions, in relation to the reactions under consideration, known to those skilled in the art.

Reaction (i) is conventionally carried out in an aprotic dipolar solvent in the presence of a base.

Reaction (ii) is conventionally carried out in a polar solvent such as methanol in the presence of a base such as LiOH or NaOH.

Reaction (iii) is conventionally carried out in dichloromethane or DMF using a peptide coupling agent such as TBTU, in the presence of an organic base such as DIEA.

Reaction (iv) is conventionally carried out with a solution of hydrobromic acid in acetic acid and in the presence of dichloromethane.

Reaction (v) is conventionally carried out in a dichloromethane/DMF mixture using an inorganic base such as KF or a supported tertiary amine such as supported triethylamine.

According to one embodiment, the compound of formula (IV) is obtained by diazomethylation of the corresponding precursor carboxylic acid.

The invention also provides a method for preparing a combinatorial library according to the invention, by simultaneously and/or sequentially carrying out the method according to the invention on a plurality of reactants.

The method according to the invention can also comprise one or more of the following optional reactions, in an appropriate order, so as to obtain the desired compound:
protection of the reactive functions,
deprotection of the reactive functions,
esterification,
saponification,
amidation,
acylation,
sulfonylation,
alkylation,
introduction of a double bond,
reduction of carboxylic acids,
salification,
ion exchange,
resolution or separation of diastereoisomers.

The optional steps are, in general, conventional reactions that are well known to those skilled in the art.

Thus, the reactive functions that it is advisable, where appropriate, to protect are generally carboxylic acid, amine, amide and hydroxyl functions.

The protection of the acid function is in particular carried out in the form of alkyl esters, or of allyl, benzyl, benzhydryl or p-nitrobenzyl esters.

The deprotection is carried out by saponification, acid hydrolysis, hydrogenolysis, or else cleavage by means of soluble palladium (O) complexes.

The protection of amines and amides is in particular carried out in the form of benzyl derivatives, in the form of carbamates, in particular allyl, benzyl, phenyl or tert-butyl carbamates, or else in the form of silyl derivatives such as tert-butyldimethyl-, trimethyl-, triphenyl- or else diphenyl-tert-butyl-silyl derivatives.

The deprotection is carried out, according to the nature of the protective group, by means of sodium or lithium in liquid ammonia, by hydrogenolysis or using soluble palladium (O) complexes, by reaction of an acid, or by the action of tetrabutylammonium fluoride.

The protection of the alcohols is carried out coventionally, in the form of ethers, of esters or of carbonates. The ethers may be alkyl ethers or alkoxyalkyl ethers, preferably methyl or methoxyethoxymethyl ethers, aryl ethers or preferably aralkyl ethers, for example benzyl ethers, or silyl ethers, for example the silyl derivatives mentioned above. The esters may be any cleavable ester known to those skilled in the art, and preferably the acetate, propionate or benzoate or p-nitrobenzoate. The carbonates may be, for example, methyl, tert-butyl, allyl, benzyl or p-nitrobenzyl carbonates.

The deprotection is carried out by means known to those skilled in the art, in particular saponification, hydrogenolysis, cleavage with soluble palladium (O) complexes, hydrolysis in acid medium or else, for the silyl derivatives, treatment with tetrabutylammmonium fluoride.

The amidation reaction is carried out starting with the carboxylic acid, by means of an activating agent such as an alkyl chloroformate or EDCI, by the action of aqueous ammonia or of an appropriate amine or of their acid salts.

The acylation and sulfonylation reactions are carried out on the hydroxyureas by the action, respectively, of an appropriate carboxylic acid halide or anhydride or of an appropriate sulfonic acid halide.

The alkylation reaction is carried out by the action, on the hydroxyl derivatives, of an alkyl halide or of an alkyl halide that is substituted, in particular with a free or esterified carboxyl radical.

The optional final introduction of a double bond is carried out by the action of a halogenated derivative of selenium, and then oxidation, according to methods known to those skilled in the art.

The reduction of acids to alcohols can be carried out by the action of a borane or via an intermediate mixed anhydride, via the action of alkali borohydride. The mixed anhydride is prepared, for example, by means of an alkyl chloroformate.

The salt formation (salification) with acids is, where appropriate, carried out by addition of an acid in the soluble phase to the compound. The salt formation with bases can concern either the compounds comprising an acid function, in particular a carboxyl function, or those comprising a sulfoxy function or those comprising a heterocycle that is acid in nature. In the first case, the process is carried out by addition of an appropriate base such as those mentioned above. In the second case, the pyridinium salt is directly obtained during the action of the $SO_3$-pyridine complex and the other salts are obtained from this pyridinium salt. In one or the other case, the process can also be carried out by ion exchange on resin. Examples of such salt formations appear hereinafter in the experimental section.

The separation of the enantiomers and diastereoisomers can be carried out according to the techniques known to those skilled in the art, in particular chromatography.

For the synthesis of the combinatorial libraries, conventional synthesis (for example, linear in solution) or conventional techniques of combinatorial chemistry (with linear or non-linear synthesis) can be used.

Illustrations of such reactions defined above are given in the preparation of the examples described hereinafter.

2. Pharmacological Properties

The products of formula (I) as defined above, and also their addition salts with acids, exhibit advantageous pharmacological properties.

The products of the present invention can thus have inhibitory properties with respect to one or more metabolic enzymes as defined above, in particular with respect to kinases or proteases.

Certain products of formula (I) of the present invention as defined above can therefore in particular have inhibitory properties with respect to certain protein kinases or with respect to proteases.

By way of proteases of interest, cathepsins B, H, J, L, N, S, T, C, V, W, K, O or O2 can be targeted, in particular those involved in diseases of cartilage and bone metabolism, and bone cancers, and most particularly cathepsin K.

The levels, the regulation and the activity of a certain number of protein kinases or proteases play a role in several human pathologies. The activity of a protein kinase or protease can in particular be associated with receptors having transmembrane domains or with intracellular proteins.

Some kinases or proteases can play a role in the initiation, the development and the completion of cell cycle events, and molecules which inhibit such kinases or proteases are thus capable of limiting undesired cell proliferations such as those observed in cancers, psoriasis, fungal growth or parasite growth (animals, protists): such molecules which inhibit these kinases or proteases are thus also capable of intervening in the regulation of neurodegenerative diseases such as Alzheimer's disease.

Certain products of formula (I) of the present invention may thus have antimitotic properties.

Certain products of formula (I) as defined above may, as kinase or protease inhibitors, have in particular the property of inhibiting osteoclast-mediated bone resorption. They may therefore be useful for the therapeutic or prophylactic treatment of diseases which are caused at least partly by an unwanted increase in bone resorption, for example osteoporosis.

Certain products of formula (I) of the present invention may thus, for example, inhibit the adhesion of osteoclasts to the surface of bone and thus the bone resorption by the osteclasts.

The bone diseases for which treatment or prevention requires the use of the compounds of formula (I) are in particular osteoporosis, hypercalcemia, osteopenia, for example caused by bone metastases, dental disorders, for example periodontitis, hyperparathyroidism, periarticular erosions in rheumatoid arthritis, Paget's disease, and osteopenia induced by immobilization. In addition, the compounds of formula (I) can be used to relieve, prevent or treat bone disorders which are caused by treatments, by glucocorticoids, therapies related to the taking of steroids or of corticosteroids, or by male or female sex hormone deficiencies.

All these disorders are characterized by a bone loss, which is based on a faulty balance between bone formation and bone destruction and which can be favorably influenced by inhibiting bone resorption by osteoclasts.

Certain products of formula (I) of the present invention may possess, in addition to their specific kinase- or protease-inhibiting properties, advantageous cellular effects such as antiproliferative properties and in particular effects on apoptosis.

It is known, by virtue of studies described in the literature such as in WO 97/20842, which is incorporated herein by reference in its entirety, that relationships exist between the cell cycle and apoptosis. Among the pathways that result in apoptosis, some are kinase- or protease-dependent.

The products of the present invention are in particular useful for tumor therapy.

The products of the invention may thus also increase the therapeutic effects of antitumor agents commonly used.

The products of formula (I) of the present invention also have antimitotic and antineurodegenerative properties.

Certain products of the present invention may be inhibitors of vasoconstrictive and hypertensive effects and may thus produce an anti-ischemic effect, or else may oppose stimulant effects on certain cell types, in particular smooth muscle cells, fibroblasts, neuronal cells and bone cells.

The products according to the present invention can thus be used in the treatment of diseases such as proliferative diseases, cancer, restenosis, inflammation; allergies, cardiovascular diseases or certain infectious diseases.

The products of the present invention may also be used in the treatment of certain gastrointestinal or gynecological disorders and in particular for a relaxing effect on the uterus.

The products of formula (I) of the present application can thus have advantageous pharmacological properties which justify their use in therapeutics.

A subject of the invention is therefore also the compounds according to the invention for their use as medicinal products, intended for the prevention or treatment of diseases mentioned above.

A subject of the invention is most particularly the pharmaceutical compositions containing, as active principle, at least one of the compounds according to the invention in combination with a pharmaceutically acceptable carrier.

The pharmaceutical compositions of the present invention as defined above can be administered buccally, parenterally or locally by topical application to the skin and the mucous membranes, or by intravenous or intramuscular injection.

These compositions may be solid or liquid and may be provided in any of the pharmaceutical forms commonly used in human medicine, such as, for example, simple or sugar-coated tablets, pills, lozenges, gelatin capsules, drops, granules, injectable preparations, ointments, creams or gels. They are prepared according to the usual methods. The active principle may be incorporated therein in excipients conventionally used in these pharmaceutical compositions, such as talc, gum arabic, lactose, starch, magnesium stearate, cocoa butter, aqueous or nonaqueous vehicles, fatty substances of animal or plant origin, paraffin derivatives, glycols, various wetting agents, dispersants or emulsifiers, or preserving agents.

The usual dosage, which can vary according to the product used, the individual treated and the condition in question, may be, for example, from about 0.05 to about 5 g per day in adults, or preferably from about 0.1 to about 2 g per day.

A subject of the invention is also the use of compounds according to the invention, for producing medicinal products intended for the prevention or treatment of diseases recalled above.

EXAMPLES

The following examples illustrate the invention without limiting it. In these examples, the following abbreviations are used:
DCM: dichloromethane
DMF: N,N-dimethylformamide
DIEA: diisopropylethylamine
DIC: diisopropylcarbodiimide
TFA: trifluoroacetic acid
EtOAc: ethyl acetate
HOBt: 1-hydroxybenzotriazole hydrate
NMM: N-methylmorpholine
TBTU: O-benzotriazol-1-yl-N,N,N',N'-tetramethyluronium tetrafluoroborate
KF: Potassium fluoride Example 1

Synthesis of the Compound of Formula II

The backbone of formula II is prepared by synthesis from the intermediate hexahydropyridazine-3-carboxylic acid (see also the description as intermediate product in documents WO-A-9955724, WO-A-9722619 and EP-A-25941).

a) Esterification of the Acid Function

The hexahydropyridazinic acid (40 g; 0.151 mol) is dissolved in 200 ml of methanol and cooled to 0° C. SOCl$_2$ (36 ml; 0.45 mol) is added dropwise. The solution becomes clear; the temperature is allowed to return very gradually to ambient temperature and the solution is then refluxed for one hour. The mixture is poured onto a DCM(200 ml)/ice(500 g)/NaHCO$_3$(60 g) mixture. The aqueous phase is extracted with DCM. The organic phase is washed with a saturated NaHCO$_3$ solution and then dried over MgSO$_4$. A colorless oil (41 g; 99%) is obtained and is used as it is.

b) Amidation of the Amine Function (Coupling with Alanine)

The Z-β-alanine (50 g; 0.183 mol) in solution in DCM/DMF (200 ml/20 ml) is cooled to 0° C.; SOCl$_2$ (25 ml; 0.32 mol) is added dropwise. The mixture is left at 0° C. for one hour with stirring. The corresponding chloride is thus obtained. The product obtained in step a) is dissolved in 150 ml of DCM at 0° C.; DIEA (33 ml; 0.19 mol) is then added, followed by the chloride previously obtained. The mixture is left for 3 hours with stirring; the temperature returns very gradually to ambient temperature. The mixture is washed successively with saturated solutions of NaHCO$_3$, KHSO$_4$ and NaCl, and then dried over MgSO$_4$. A yellow oil is obtained, which is purified by chromatography (1300 g silica column; eluent: 90/10 DCM/EtOAc).

c) Deprotection of the Amine Functions by Hydrogenolysis

The compound obtained in step b) (26 g; 0.054 mol) is dissolved in 250 ml of DCM/250 ml of MeOH; Pd/C (2.7 g) is then added. The mixture is left for 12 hours under a pressure of between 1900 and 1950 mbar. The palladium is changed in the course of the reaction. The filtrate is evaporated to dryness. White crystals (8.5 g; 73%) are obtained. LC-MS analysis confirms that it is indeed the desired compound of formula II (n=2).

The overall reaction scheme is represented below (Z representing the group $C_6H_5CH_2OC(O)-$).

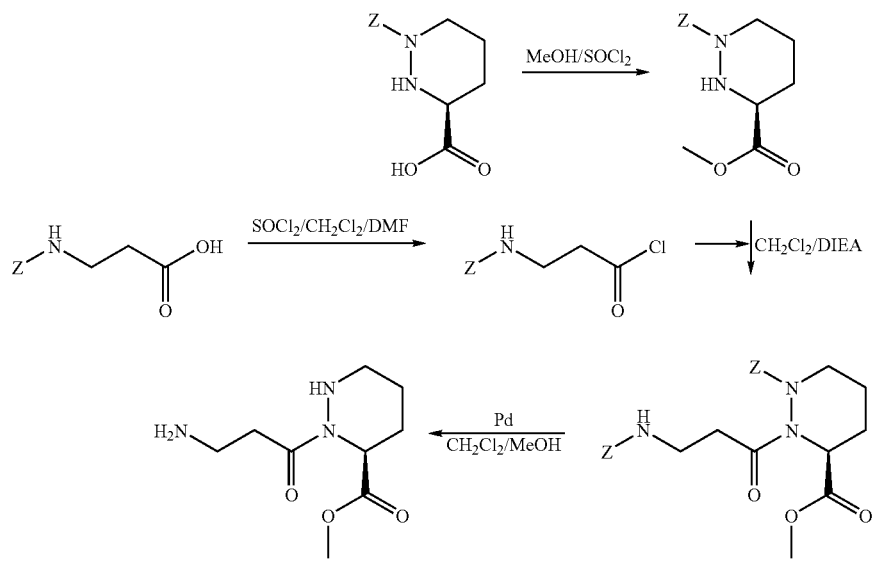

Example 2

Synthesis of the Compounds

The overall synthesis scheme for the desired compounds is given below (with R$_3$ obtained by reaction of an anhydride). The combinatorial library is obtained by conventional synthesis in solution.

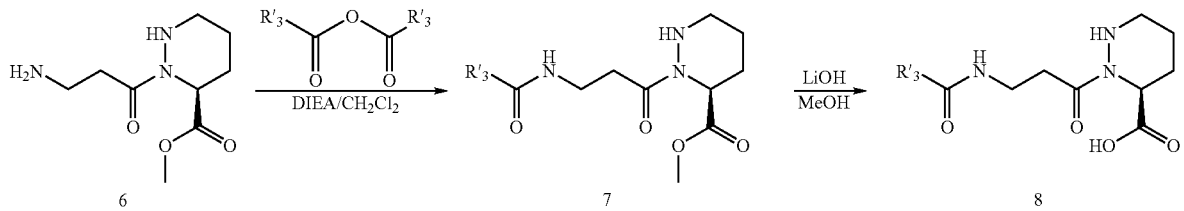

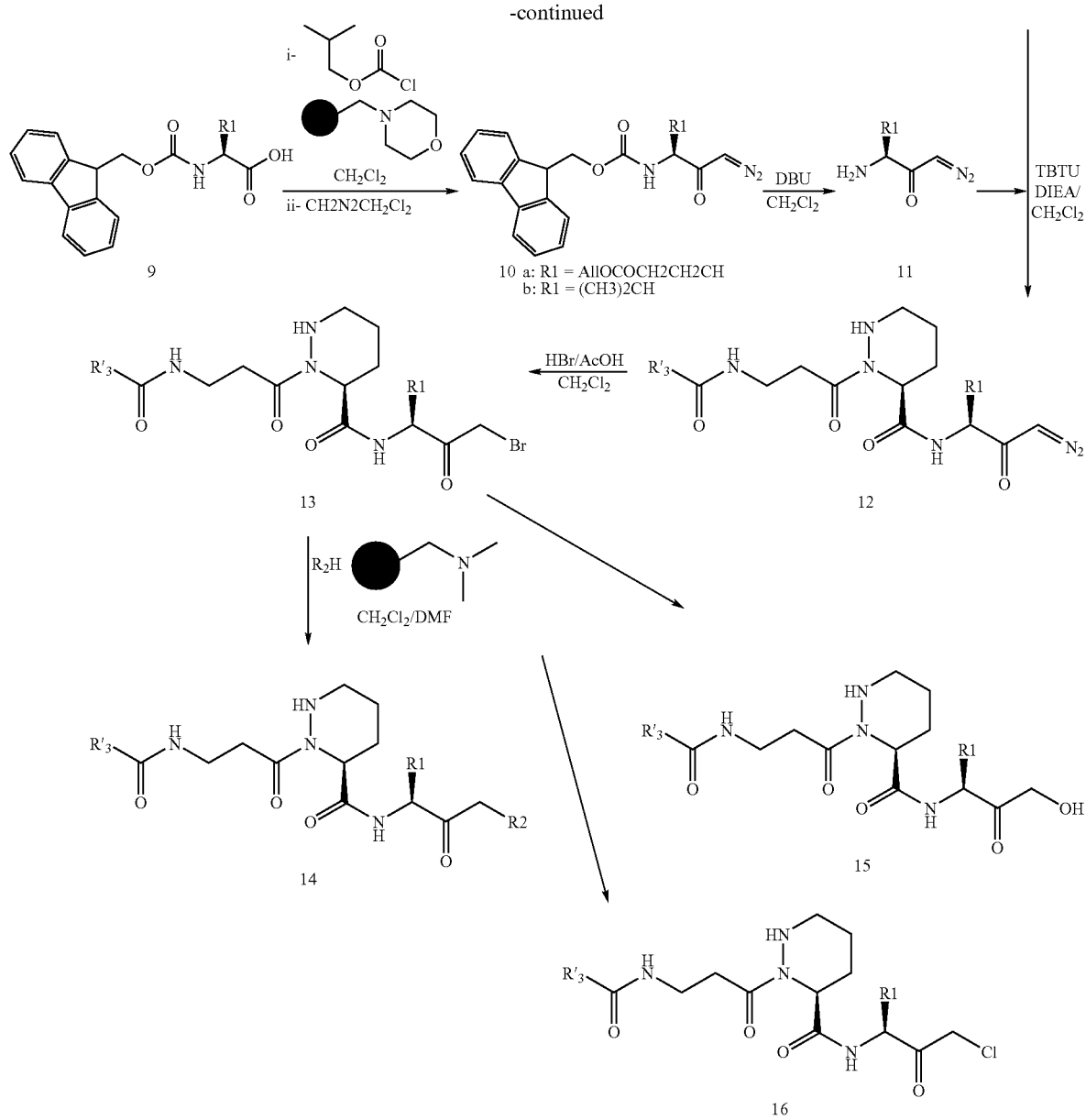

a) Acylation of the Primary Amine 2.1 ml (10.5 mmol; 1.5 eq.) of isovaleric acid anhydride in 10 ml CH$_2$Cl$_2$ and 2.2 ml of DIEA are added successively to a solution of 1.5 g (7 mmol) of amine 6 in 15 ml of CH$_2$Cl$_2$. After reaction for one hour at ambient temperature, the mixture is poured into saturated NaHCO$_3$ solution. After separation by settling out, the aqueous phase is extracted with CH$_2$Cl$_2$. The combined organic phases are washed with water, dried (MgSO$_4$), and concentrated under vacuum. The crude product is purified by chromatography on silica gel (200 g) using 95/5 CH$_2$Cl$_2$/MeOH as eluent. 1.2 g of compound 7 is obtained (yield 56%).

b) Saponification of the Ester 0.192 g of LiOH (8 mmol; 2 eq.) is added to a solution of 1.2 g (4 mmol) of ester 7 in 12 ml of MeOH. After reaction for two hours at ambient temperature, the methanol is removed under vacuum. The white solid is dissolved in 5 ml of water. The pH of the solution is neutralized with 2N HCl and the solution is lyophilizied. The hygroscopic crude acid 8 is directly used for the other step.

c) Synthesis of the Diazoketone c1: diazoketone 10a: 1.02 g of amino acid 9 (L-Val(OH)) protected with Fmoc (3 mmol, 1 eq.) and then 0.40 ml of isobutyl chloroformate (3.1 mmol, 1.03 eq.) are added, at −10° C. under nitrogen, to a suspension of 3 g (6 mmol, 3 eq.) of N-methylmorpholine supported on polystyrene (Argonaut, 2 mmol/g) in 29 ml of CH$_2$Cl$_2$. The reaction mixture is stirred for 1 hour at −10° C. and then filtered. The resin is washed twice with 15 ml of cold CH$_2$Cl$_2$. The solution is cooled again to −10° C. and 20 ml of a 0.3M diazomethane solution (6 mmol, 2 eq.) are added under nitrogen. After reaction for one hour at −10° C., the solution is concentrated under vacuum. 0.96 g of a yellow solid, corresponding to diazoketone 10a (yield 88%), is isolated.

c2: diazoketone 10b: The procedure is substantially identical to that of the preceding paragraph. It is as follows. 4 ml of N-methylmorpholine (36 mmol, 1.2 eq.) followed by 4.3 ml of isobutyl chloroformate (33 mmol, 1.1 eq.) are added, at −10° C. under nitrogen, to a solution of 12.3 g of amino acid 9 (L-Glu- allyl ester protected with Fmoc) (30 mmol) in 100 ml of $CH_2Cl_2$. The reaction mixture is stirred for 1 hour at —10° C. and then filtered. The resin is washed twice with 15 ml of cold $CH_2Cl_2$. The solution is cooled again to −10° C. and two equivalents of a solution of diazomethane are added under nitrogen. After reaction for one hour at −10° C., the solution is concentrated under vacuum. The crude product is purified on silica gel (500 g) using 95/5 $CH_2Cl_2$/MeOH as eluent. 10.4 g of diazoketone 10b are obtained (yield 85%).

d) Coupling of the Diazoketone d1: deprotection of diazoketone 10: A solution of diazoketone 10 in $CH_2Cl_2$ (3 ml/mmol) is treated with 2.1 equivalents of diazabicycloundecene (DBU) at ambient temperature. After 30 min, the reaction mixture is directly applied to a column of silica gel. The column is washed with $CH_2Cl_2$, and then the free amine is eluted with 90/10 $CH_2Cl_2$/MeOH as eluent. After concentration under vacuum at 25° C., the residue 11 is directly used in the coupling reaction which follows.

d2: coupling: 1 equivalent of amine 11 in $CH_2Cl_2$ (4 ml/mmol) are added, under nitrogen and at ambient temperature, to a solution of 1.1 equivalents of acid 8 in DMF (4 ml/mmol), followed by 1.1 equivalents of TBTU (O-(benzotriazol-1-yl)-N,N,N',N'-tetramethyluronium tetrafluoroborate) and 2 equivalents of DIEA (diisopropylethylamine). The reaction mixture is stirred under nitrogen for 4 hours and then poured into a saturated sodium bicarbonate solution. The mixture is extracted twice with EtOAc. The combined organic phases are washed with water, dried over $MgSO_4$, and then concentrated under vacuum. The crude product is purified on silica gel so as to provide the desired compound 12.

e) Bromination of the Diazoketone

A solution of diazoketone 12 in $CH_2Cl_2$ (15 ml/mmol) is treated with a solution of 35% HBr/acetic acid (30/70) (0.42 ml/mmol) at ambient temperature. After reaction for one hour, the same amount of the HBr/AcOH solution is added and the reaction mixture is maintained for 1 hour with stirring. The reaction mixture is poured into a saturated sodium bicarbonate solution and then extracted with $CH_2Cl_2$. The organic phase is washed with water, dried over $MgSO_4$, and then concentrated under vacuum to provide the desired bromoketone 13. It is also possible to envision flash chromatography on silica gel using 98/2 $CH_2Cl_2$/MeOH as eluent.

f) Substitution of the Bromine f1: substitution with a nucleophile: A dimethylaminomethylpolystyrene resin (3–4 mmol/g) (~2 equivalents) and then 2 equivalents of nucleophile $R_2H$ are added to a solution of bromoketone 13 in $CH_2Cl_2$ (~5 ml/mmol). The reaction mixture is stirred overnight. The reaction mixture is filtered through SPE silica gel and the filtrate is concentrated under vacuum. The compounds exhibiting a purity of less than 80% are purified by flash chromatography on silica gel to provide the desired compound 14.

f2: substitution with hydroxyl: Displacement of the bromine with the monoamide of pyridazine-2,3-dicarboxylic acid under the above conditions results in the formation of α-hydroxyketone 15 as sole product with a quantitative yield.

f3: substitution with another halogen: Displacement of the bromine with 2,2-pyridylacetic acid hydrochloride under the above conditions results in the formation of α-chloroketone 16 as the sole product (yield 56%).

All the products obtained were subjected to LC-MS analysis.

The following table groups together the examples.

| Example | Structure | Mass |
|---|---|---|
| 1 | 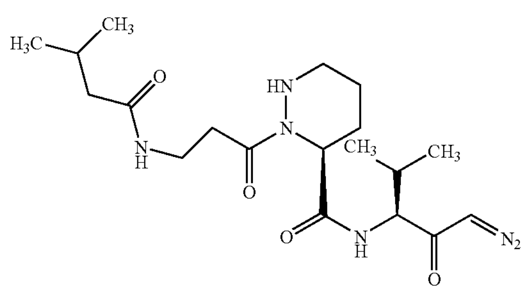 | 408.5 |
| 2 | 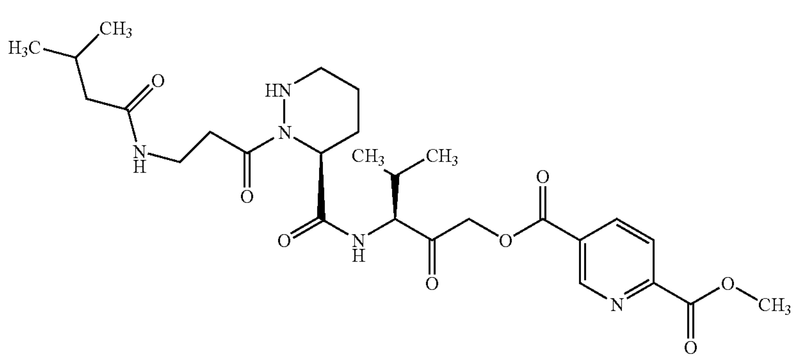 | 561.64 |

-continued

| Example | Structure | Mass |
|---|---|---|
| 3 | 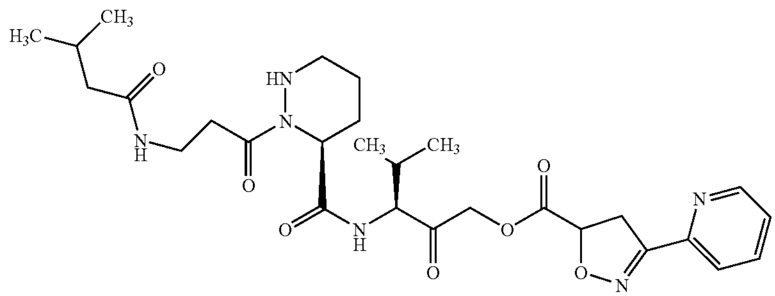 | 572.67 |
| 4 | 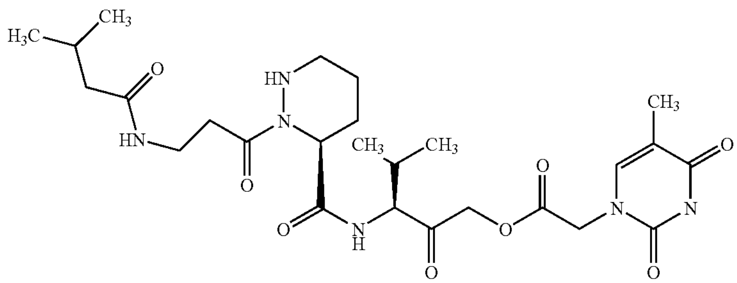 | 564.64 |
| 5 | 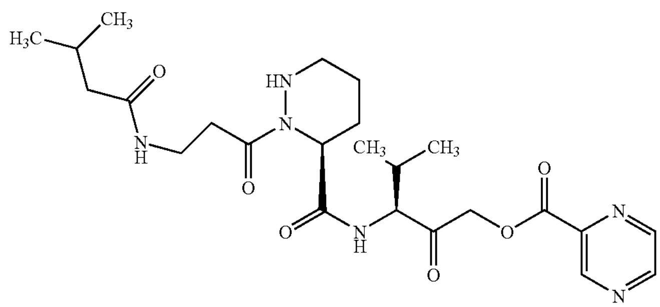 | 504.59 |
| 6 | 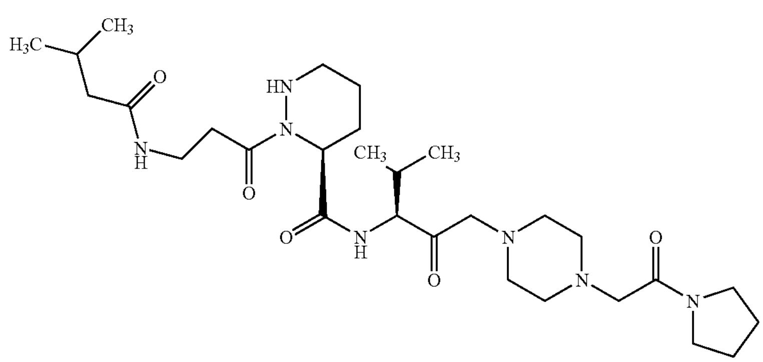 | 577.77 |
| 7 | 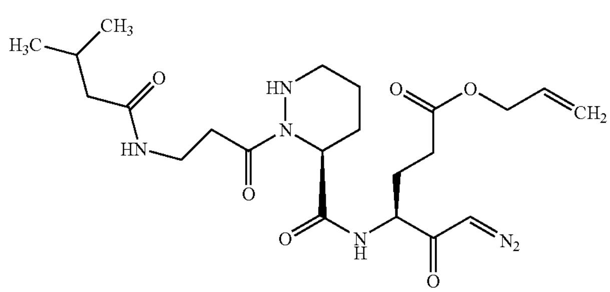 | 478.55 |

| Example | Structure | Mass |
|---|---|---|
| 8 | 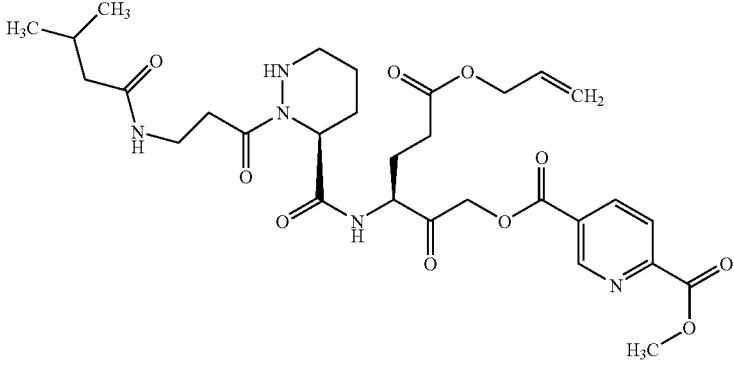 | 631.69 |
| 9 | 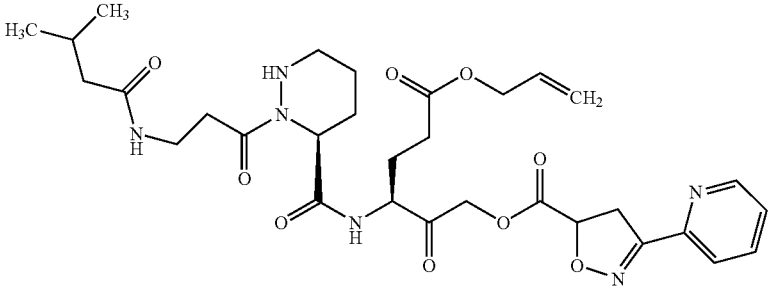 | 642.72 |
| 10 | 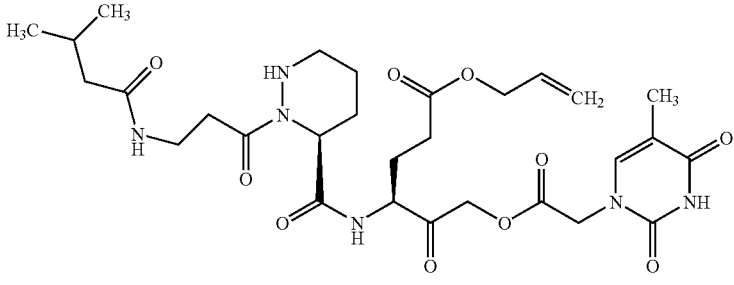 | 634.6 |
| 11 | 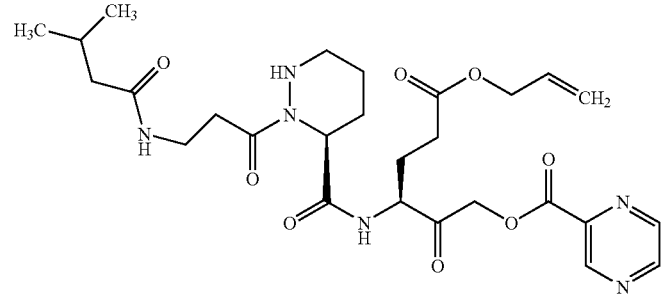 | 572.64 |

-continued
| Example | Structure | Mass |
|---|---|---|
| 12 | 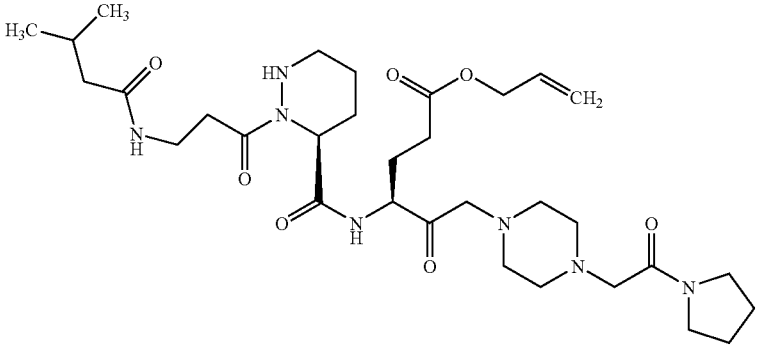 | 674.82 |
| 13 | 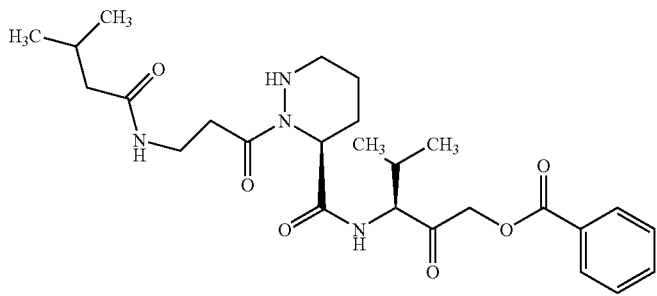 | 502.62 |
| 14 | 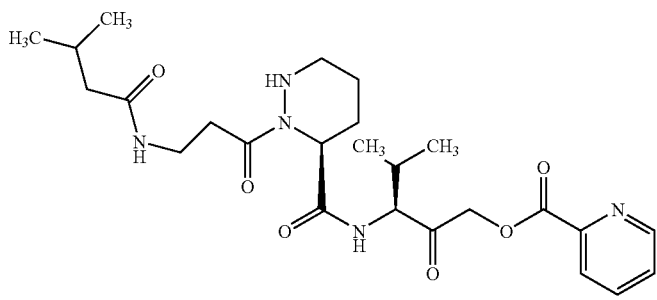 | 503.6 |
| 15 | 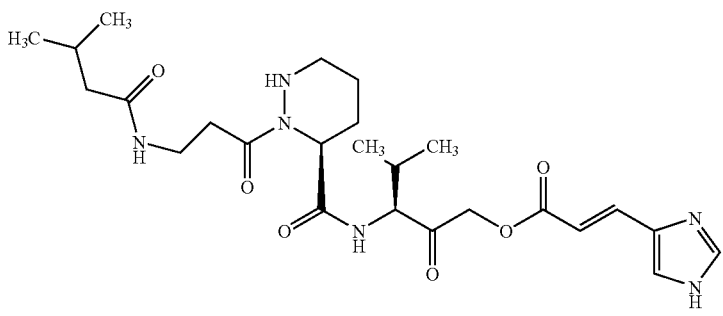 | 518.62 |
| 16 | 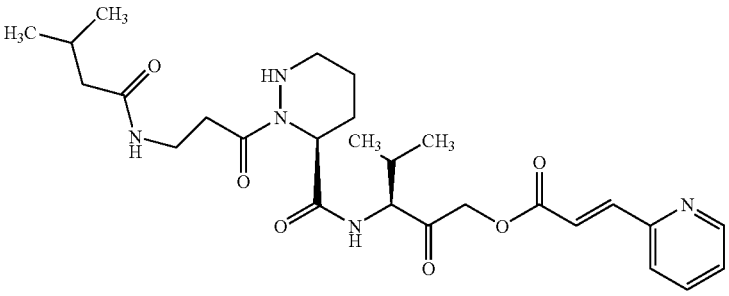 | 529.64 |

-continued
| Example | Structure | Mass |
|---------|-----------|------|
| 17 | 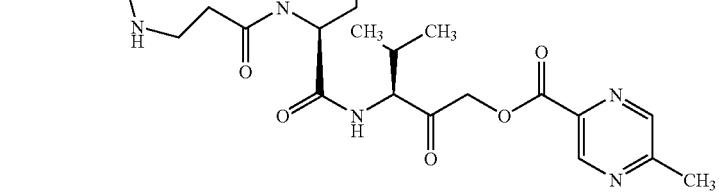 | 518.62 |
| 18 | 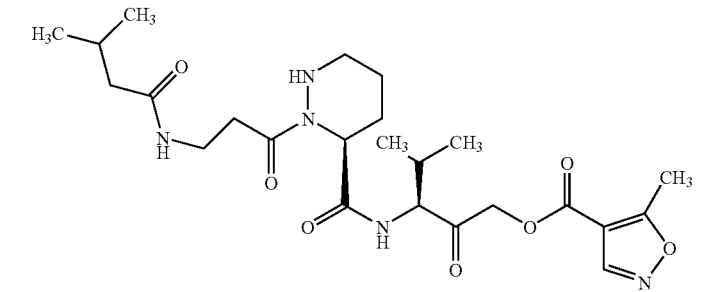 | 507.59 |
| 19 | 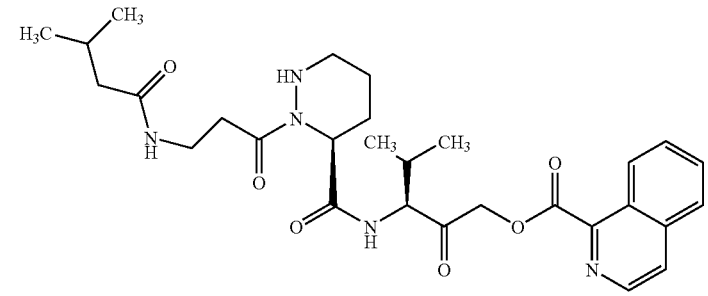 | 553.66 |
| 20 | 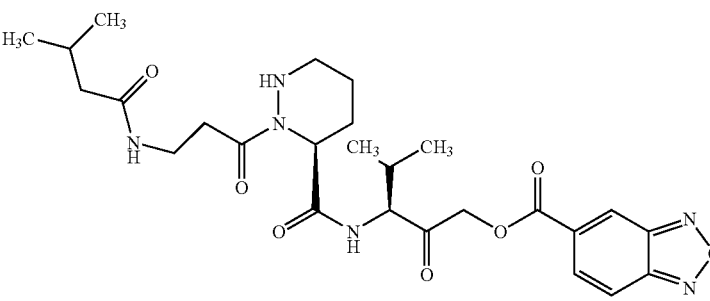 | 544.61 |
| 21 | 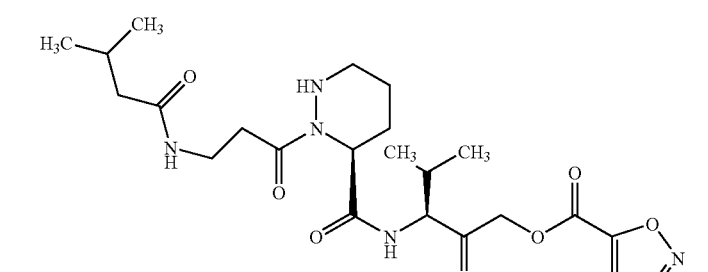 | 493.56 |

US 7,034,022 B2
29    30
-continued
| Example | Structure | Mass |
|---|---|---|
| 22 | 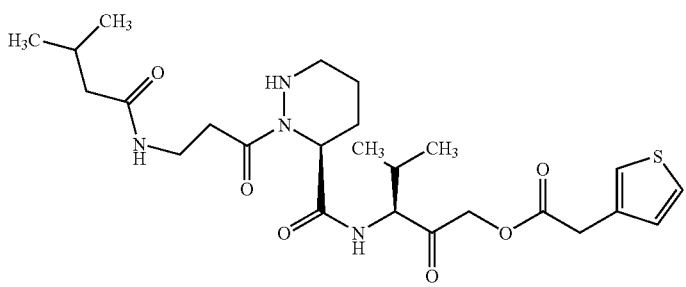 | 522.67 |
| 23 | 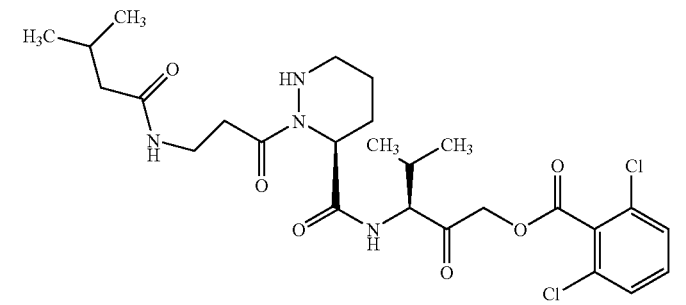 | 571.51 |
| 24 | 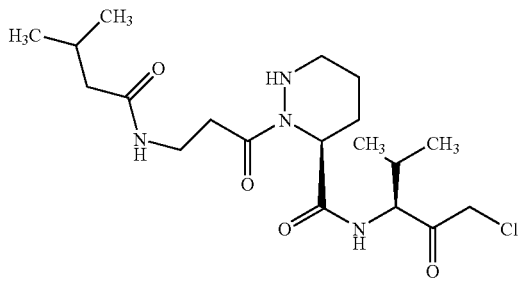 | 416.95 |
| 25 | 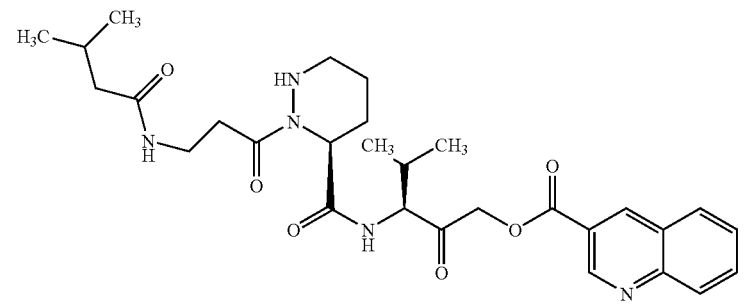 | 553.66 |
| 26 | 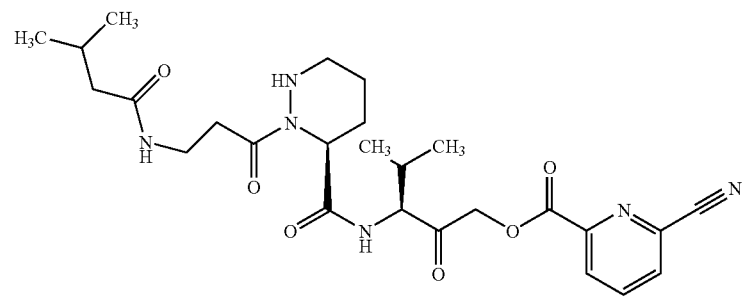 | 528.61 |

-continued

| Example | Structure | Mass |
|---|---|---|
| 27 | 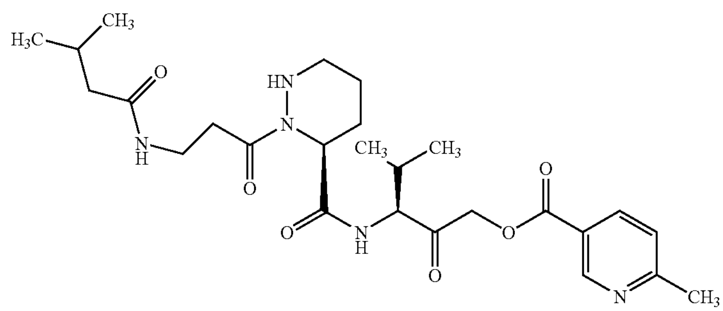 | 517.63 |
| 28 | 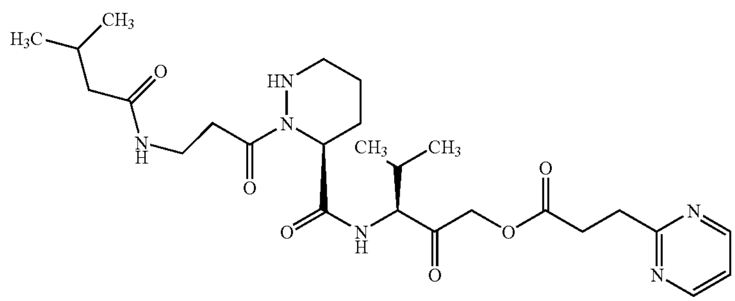 | 532.65 |
| 29 | 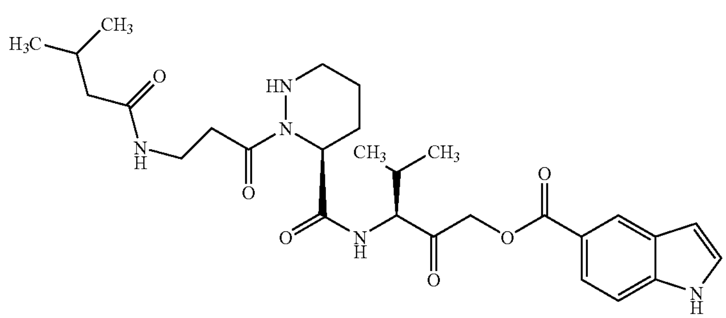 | 541.65 |
| 30 | 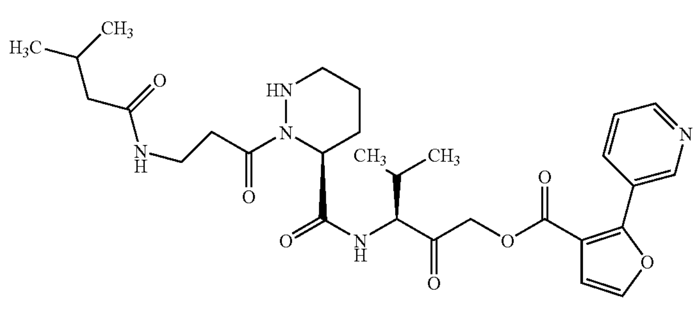 | 569.66 |

| Example | Structure | Mass |
|---|---|---|
| 31 | 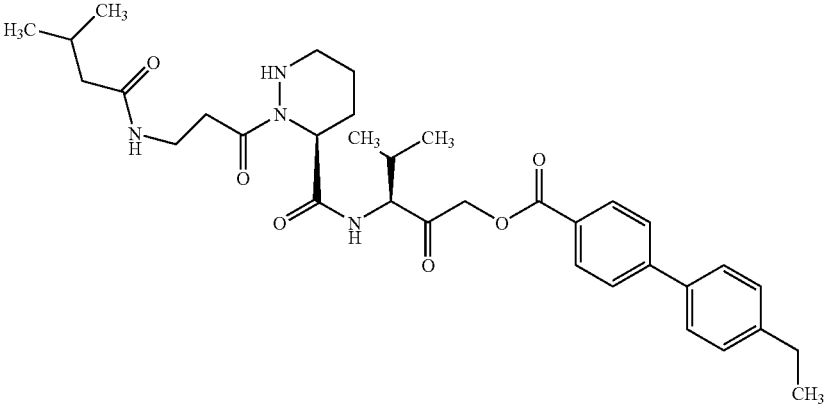 | 606.77 |
| 32 | 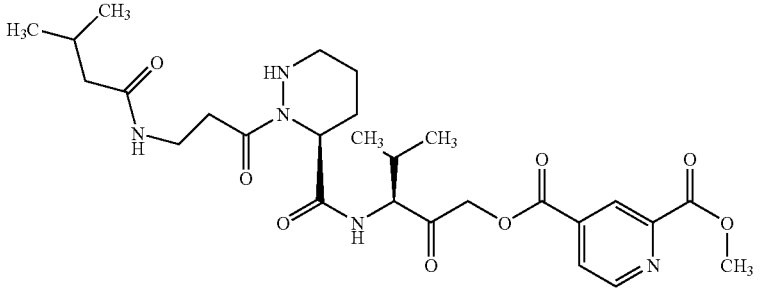 | 561.64 |
| 33 | 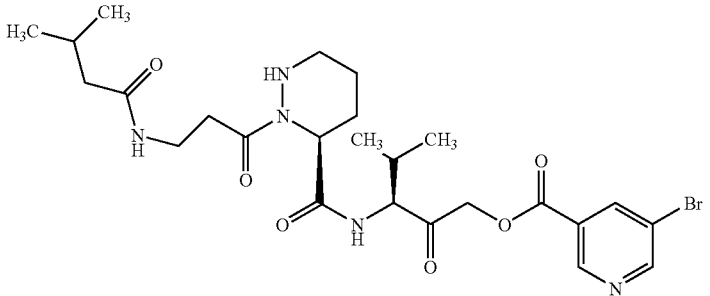 | 582.5 |
| 34 | 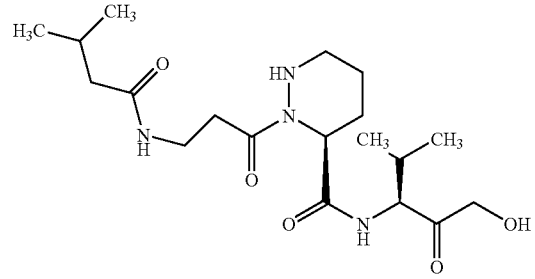 | 398.51 |

-continued

| Example | Structure | Mass |
|---|---|---|
| 35 | 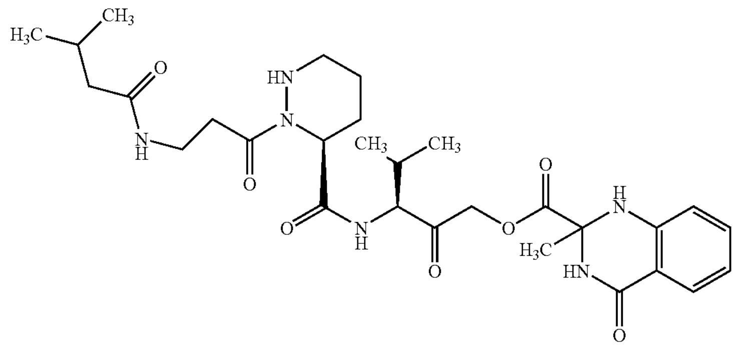 | 586.69 |
| 36 | 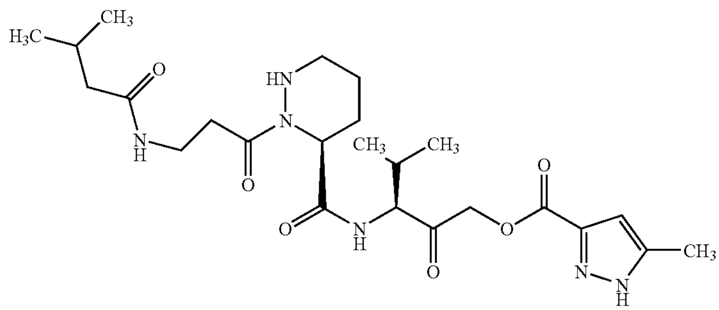 | 506.61 |
| 37 | 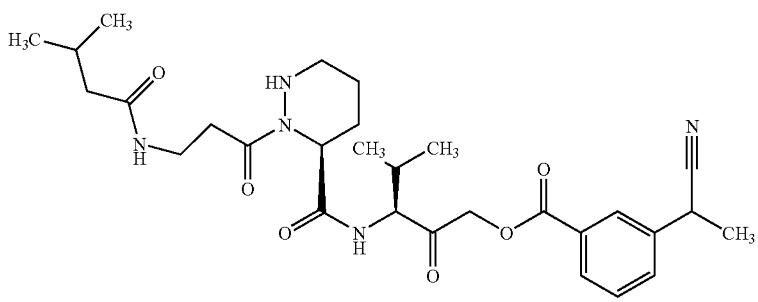 | 555.68 |
| 38 | 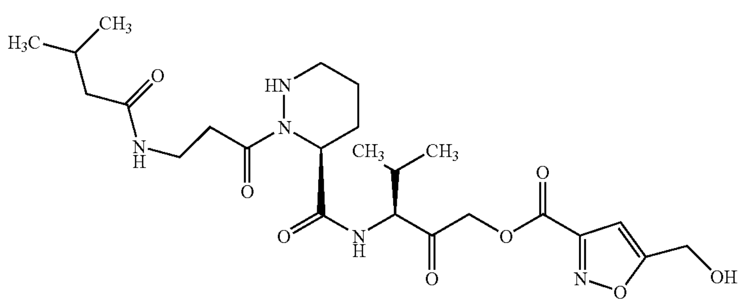 | 523.59 |
| 39 | 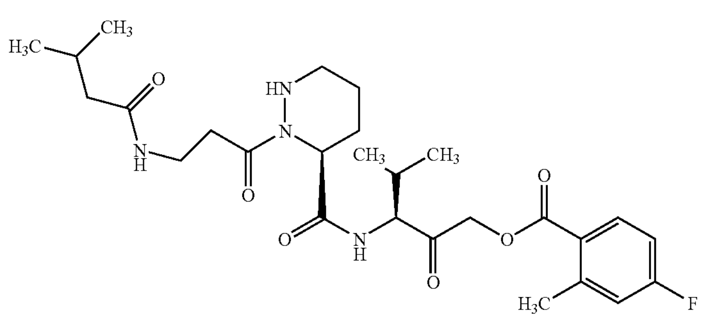 | 534.63 |

| Example | Structure | Mass |
|---|---|---|
| 40 | 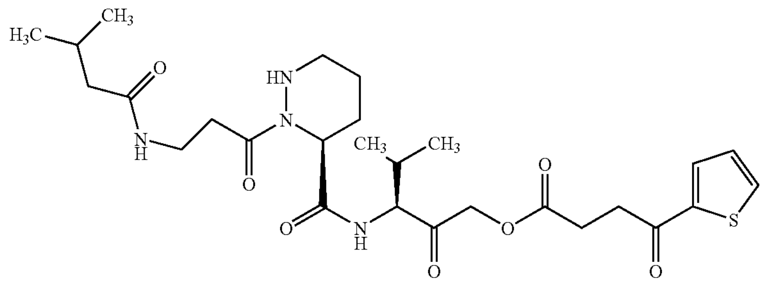 | 564.71 |
| 41 | 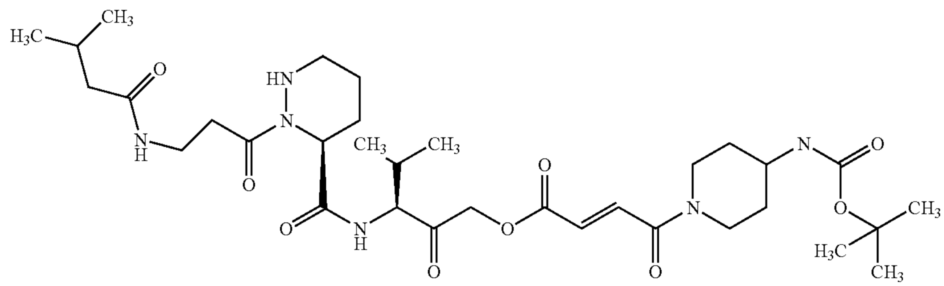 | 678.83 |
| 42 | 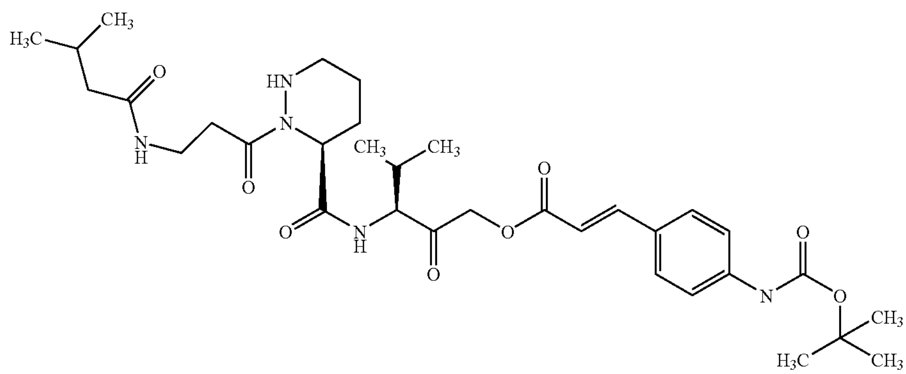 | 643.79 |
| 43 | 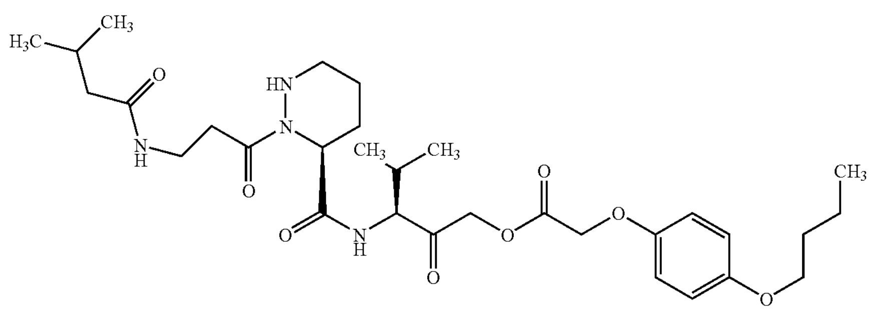 | 604.75 |
| 44 | 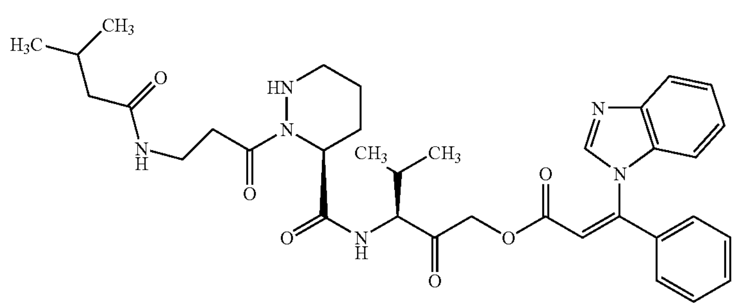 | 644.78 |

-continued

| Example | Structure | Mass |
|---|---|---|
| 45 | 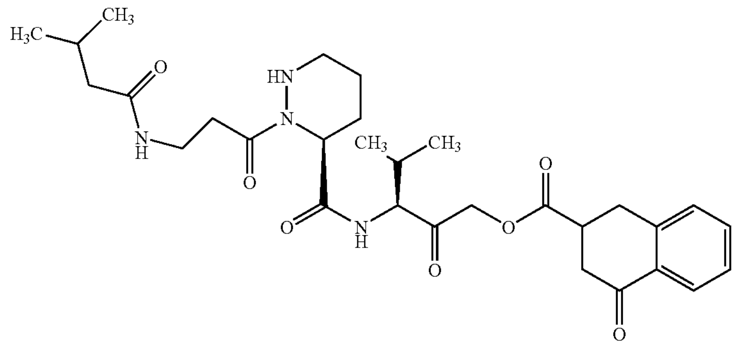 | 570.69 |
| 46 | 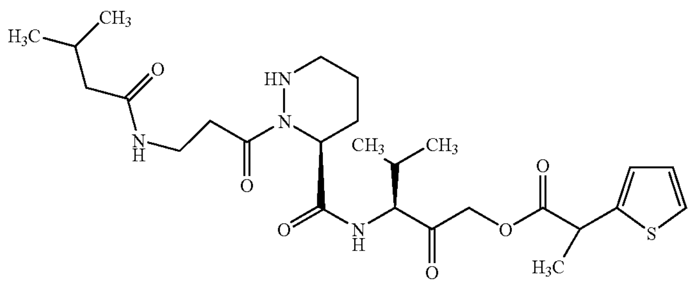 | 536.7 |
| 47 | 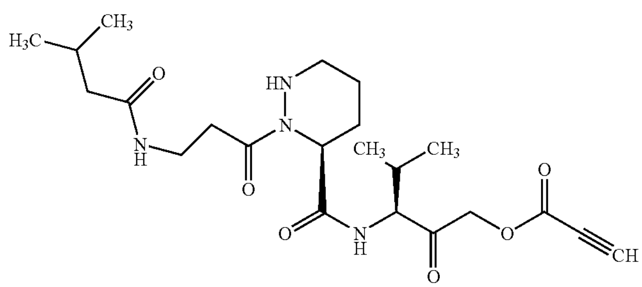 | 450.54 |

Pharmacological Study of the Products of the Invention

Example 3

Study of the Inhibition of Cathepsin K

The enzyme reaction is carried out in 96-well Costar® plates. The kinetics of the catalytic reaction are measured and the percentage inhibition determined after incubation for one hour at 37° C. The calculation is derived from the fluorescence measurement (use of a Spectrafluor Plus from the company Tecan).

The reaction medium (200 µl) is as follows:
- 170 µl of acetate buffer (100 mM, pH 5.5) containing EDTA (5 mM) and L-cysteine (20 mM). The reaction medium is preincubated at 37° C. and the following solutions are then added.
- 10 µl of test compound ($2 \times 10^{-5}$ M in DMSO, diluted stock solution from 2% to 20% (v/v) according to the solubility of the compound) at a concentration of 1 µM, or 10 µl of solvent as control.
- 10 µl of substrate (Z-Val-Arg-AMC) solution in DMSO/ED (4% v/v), at a concentration of 20 mM.
- 10 µl of enzyme solution at 100 ng/ml in 0.1% Brij® (1.4% v/v Brij/acetate buffer), or 10 µl of solvent as control. A preincubation for 5 min is carried out just before the enzyme reaction. The final concentration is 5 ng/ml.

The starting point is the addition of the enzyme.

All the measurements are duplicated. The percentage inhibition (at 1 µM) and the $IC_{50}$ are determined.

The products of examples 2, 7, 8, 9, 10, 17, 18, 19, 20, 21, 24, 29, 42 and 47 exhibit an $IC_{50}$ of less than Example 4

Pharmaceutical Composition

Tablets corresponding to the formula below are prepared:
Compound according to the invention 500 mg
Excipient for a tablet with a final weight of 1 g
(excipient in detail: lactose, talc, starch, magnesium stearate).

What is claimed is:

1. A compound of formula (I)

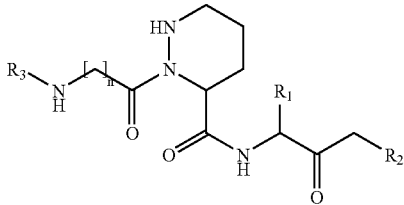

wherein n is an integer from 0 to 6;

$R_1$ is a linear or branched alkyl of 1 to 6 carbon atoms, aryl containing from 6 to 10 carbon atoms, aralkyl containing from 7 to 11 carbon atoms, or a saturated or unsaturated monocyclic or bicyclic heterocyclic group, wherein said alkyl, aryl, aralkyl, or heterocyclic group is each optionally substituted with one to three substituents independently selected from OH, oxo, SH, $NH_2$, $NO_2$, cyano, carboxyl, carboxyl esterified with $C_1$–$C_4$ alkyl or $C_2$–$C_4$ alkenyl, carbamoyl, halogen, trifluoromethyl, linear or branched alkoxy containing from 1 to 6 carbon atoms, acyl containing from 2 to 6 carbon atoms, aryl, aralkyl, or a saturated or unsaturated monocyclic or bicyclic heterocyclic group;

$R_2$ together with the carbon to which it is linked is C=$N_2$, or $R_2$ is selected from halogen,
hydroxyl,
—O—$(CH_2)_m$—R,
—S—$(CH_2)_m$—R,
—OC(O)—$(CH_2)_m$—R, or
—NRR',
wherein m is an integer from 0 to 6, and wherein when m is greater than or equal to 2 a double bond is optionally present;

said $(CH_2)_m$ is optionally substituted with a linear or branched alkyl of 1 to 6 carbon atoms, aryl containing from 6 to 10 carbon atoms, aralkyl containing from 7 to 11 carbon atoms, or a saturated or unsaturated monocyclic or bicyclic heterocyclic group;

R is selected from hydrogen when m is other than 0,
hydroxyl,
thiol,
cyano,
linear or branched alkoxy containing from 1 to 6 carbon atoms,
aryloxy, or
aralkoxy,
  wherein said aryloxy or aralkoxy ring is each optionally substituted with one to three substituents independently selected from OH, SH, $NH_2$, $NO_2$, cyano, carboxyl, carboxyl esterified with a $C_1$–$C_4$ alkyl, carbamoyl, —NHC(O)O—$C_{1-4}$-alkyl, halogen, trifluoromethyl, linear or branched alkyl containing from 1 to 6 carbon atoms, linear or branched alkoxy containing from 1 to 6 carbon atoms, acyl containing from 2 to 6 carbon atoms, or a saturated or unsaturated moncyclic or bicyclic heterocyclic group;
cycloalkyl having from 3 to 6 carbon atoms;
saturated or unsaturated monocyclic or bicyclic heterocyclic group,
  wherein said heterocyclic group is optionally substituted with one to three substituents independently selected from OH, oxo, SH, $NH_2$, $NO_2$, cyano, carboxyl, carboxyl esterified with a $C_1$–$C_4$ alkyl, carbamoyl, —NHC(O)O—$C_{1-4}$-alkyl, halogen, trifluoromethyl, linear or branched alkyl containing from 1 to 6 carbon atoms, linear or branched alkoxy containing from 1 to 6 carbon atoms, acyl containing from 2 to 6 carbon atoms, aryl, aralkyl, or a saturated or unsaturated monocyclic or bicyclic heterocyclic group,
    wherein said alkyl, aralkyl, or heterocyclic group is each optionally substituted with one to three substituents independently selected from OH, SH, $NH_2$, $NO_2$, cyano, carboxyl, carboxyl esterified with a $C_1$–$C_4$ alkyl, carbamoyl, halogen, trifluoromethyl;
aryl containing from 6 to 10 carbon atoms, or aralkyl containing from 7 to 11 carbon atoms,
  wherein the ring of said aryl or aralkyl is optionally substituted with one to three substituents independently selected from OH, SH, $NH_2$, $NO_2$, cyano, carboxyl, carboxyl esterified with a $C_1$–$C_4$ alkyl, carbamoyl, —NHC(O)O—$C_{1-4}$-alkyl, halogen, trifluoromethyl, linear or branched alkyl containing from 1 to 6 carbon atoms, linear or branched alkoxy containing from 1 to 6 carbon atoms, acyl containing from 2 to 6 carbon atoms, or a saturated or unsaturated monocyclic or bicyclic heterocyclic group,
    wherein said alkyl or heterocyclic group is each optionally substituted with one to three substituents independently selected from OH, SH, $NH_2$, $NO_2$, cyano, carboxyl, carboxyl esterified with a $C_1$–$C_4$ alkyl, carbamoyl, halogen, or trifluoromethyl;
$NR_4R_5$, wherein $R_4$ is hydrogen, or linear or branched alkyl having from 1 to 6 carbon atoms, and $R_5$ is hydrogen, linear or branched alkyl having from 1 to 6 carbon atoms, or aryl;
R' is as defined for R, wherein R and R' are identical or different, or R and R' together with the nitrogen atom to which they are linked form a nitrogenous heterocycle,
  wherein said heterocycle is optionally substituted with one to three substituents independently selected from OH, SH, $NH_2$, $NO_2$, cyano, carboxyl, carboxyl esterified with a $C_1$–$C_4$ alkyl, carbamoyl, halogen, trifluoromethyl, linear or branched alkyl containing from 1 to 6 carbon atoms, linear or branched alkoxy containing from 1 to 6 carbon atoms, acyl containing from 2 to 6 carbon atoms, or a saturated or unsaturated monocyclic or bicyclic heterocyclic group,
    wherein said heterocyclic group is optionally linked by a bond, —C(O)—, or —$CH_2$—C(O)— to said nitrogenous heterocycle;

$R_3$ is —C(O)—R'$_3$, —C(O)—NH—R'$_3$, —C(S)—NH—R'$_3$ or —$SO_2$—R'$_3$,
  wherein R'$_3$ is a linear or branched alkyl of 1 to 6 carbon atoms, aryl containing from 6 to 10 carbon atoms or aralkyl containing from 7 to 11 carbon atoms, or a saturated or unsaturated monocyclic or bicyclic heterocyclic group; or an enantiomer, a racemate, a diastereoisomer, or a mixture in any combination thereof, or a pharmaceutically acceptable salt thereof.

2. The compound according to claim 1, wherein n is 2.

3. The compound according to claim 1, wherein $R_1$ is optionally substituted alkyl.

4. The compound according to claim 3, wherein n is 2.

5. The compound according to claim 1, wherein $R'_3$ is alkyl.

6. The compound according to claim 5, wherein n is 2.

7. The compound according to claim 6, wherein $R_1$ is optionally substituted alkyl.

8. The compound according to claim 1, wherein $R_2$ is
—O—$(CH_2)_m$—R,
—S—$(CH_2)_m$—R,
—OC(O)—$(CH_2)_m$—R, or
—NRR',
wherein
m is an integer from 0 to 2 and when m is 2 a double bond is optionally present;
R is
a saturated or unsaturated monocyclic or bicyclic heterocyclic group,
aryl containing from 6 to 10 carbon atoms, or
aralkyl containing from 7 to 11 carbon atoms,
wherein the ring of said heterocyclic group, aryl or aralkyl is each optionally substituted, or
R' is as defined for R, wherein R' and R are identical or different, or R' and R, together with nitrogen atom to which they are linked, form a nitrogenous heterocycle,
wherein said heterocycle is optionally substituted.

9. The compound according to claim 8, wherein n is 2.

10. The compound according to claim 9, wherein $R_1$ is optionally substituted alkyl.

11. The compound according to claim 1 having the stereochemistry

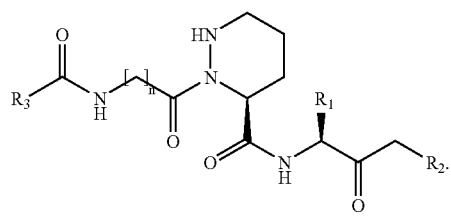

12. A method for the treatment of a bone disease selected from the group consisting of osteoporosis, hypercalcemia, osteopenia, gingival disease, arthritis, Paget's disease and bone cancer in a patient comprising to said patient a therapeutically effective amount of a compound of formula I according to claim 1.

13. A method for the inhibition K in vitro, comprising contacting said cathepsin K with a compound of formula 1 according to claim 1.

14. A pharmaceutical composition comprising a pharmaceutically acceptable carrier and a compound of formula I according to claim 1, or a stereoisomer, an enantiomer, a racemate, a diastereomers, or a mixture in any combination thereof, or a pharmaceutically acceptable salt thereof.

15. A method for the preparation of a pharmaceutical composition to treat a disease ameliorated by inhibition of a kinase or a protease selected from the group consisting of aspartic protease, serine protease, cysteine protease, and metalloprotease comprising mixing a pharmaceutically acceptable carrier and a therapeutically effective amount of a compound of formula (I) according to claim 1.

16. A process for preparing a compound of formula I according to claim 1 comprising the steps of:

(i) reacting of a compound of formula (II) wherein n is as defined in claim 1,

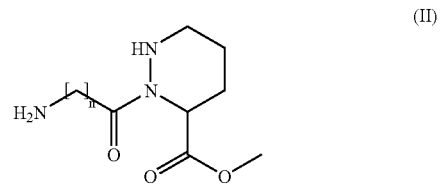

with an anhydride, acid chloride, sulfonyl chloride, carbamoyl chloride, chloroformate, isocyanate or isothiocyanate of the group $R_3$, wherein $R_3$ is as defined in claim 1, to afford a compound of formula (III),

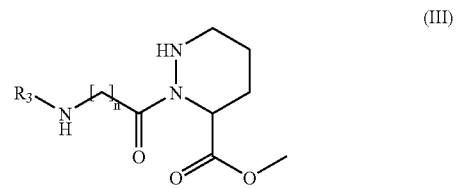

(ii) saponifying the compound of formula III to afford a 3-carboxylic acid of formula (IIIa),

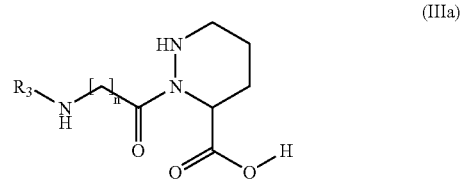

(iii) reacting the compound of formula (IIIa) with a compound of formula (IV),

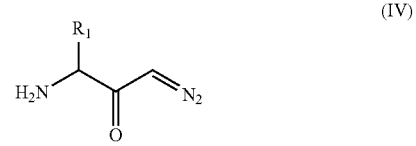

wherein $R_1$ is as defined in claim 1, to afford a compound of formula (V),

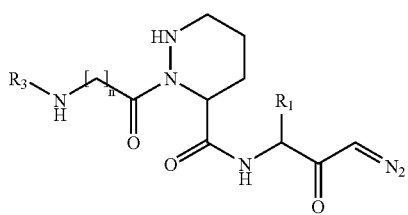

(V)

(iv) optionally halogenating the compound of formula (V) to afford a compound of formula (VI)

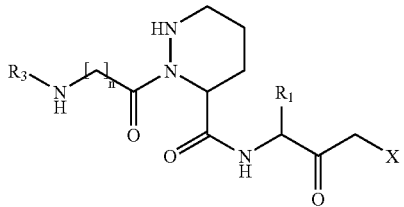

(VI)

wherein X is halogen, and (v) optionally reacting the compound of formula (VI) with a compound of the formula R₂H, wherein R₂ is as defined in claim 1, to afford a compound of formula (I),

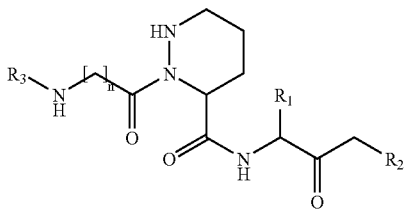

(I)

or (vi) optionally reacting a compound of formula (V) with the monoamide of pyridazine-2,3-dicarboxylic acid to afford a compound of formula (I) wherein R₂ is OH.

17. The process according to claim 16 wherein the compound of formula (IV) is obtained by diazomethylation of the corresponding precursor carboxylic acid.

18. The process according to claim 16 comprising simultaneously or sequentially performing the steps of said process on a plurality of reactants.

19. The process according to claim 16, wherein a combinatorial library of compounds of formula (I) is prepared.

* * * * *